(12) United States Patent
Brown

(10) Patent No.: US 6,207,063 B1
(45) Date of Patent: *Mar. 27, 2001

(54) BLOOD PROCESSING SYSTEMS AND METHODS USING APPARENT HEMATOCRIT AS A PROCESS CONTROL PARAMETER

(75) Inventor: Richard I. Brown, Northbrook, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/527,148

(22) Filed: Mar. 16, 2000

Related U.S. Application Data

(63) Continuation of application No. 08/960,674, filed on Oct. 30, 1997, now Pat. No. 6,059,979, which is a continuation of application No. 08/473,316, filed on Jun. 7, 1995, now Pat. No. 5,730,883, which is a continuation-in-part of application No. 08/097,967, filed on Jul. 26, 1993, now abandoned, which is a continuation-in-part of application No. 07/965,088, filed on Oct. 22, 1992, now Pat. No. 5,370,802, which is a continuation-in-part of application No. 07/814,403, filed on Dec. 23, 1991, now abandoned.

(51) Int. Cl.$^7$ .......................... B01D 17/12; B01D 17/038
(52) U.S. Cl. ................... 210/739; 210/87; 210/145; 210/194; 210/512.1; 210/787; 210/805; 494/10; 494/37; 604/4.01
(58) Field of Search ............................. 210/85–87, 94, 210/96.1, 143, 145, 149, 194, 195.1, 257.1, 360.1, 512.1, 739, 745, 767, 787, 789, 805; 604/4.01, 5.01; 364/413.07, 554, 555, 564, 567, 569; 128/DIG. 13; 422/74; 494/6, 10, 37

(56) References Cited

U.S. PATENT DOCUMENTS

| | | |
|---|---|---|
| 3,916,892 | 11/1975 | Latham, Jr. . |
| 4,447,191 | 5/1984 | Bilstad et al. . |
| 4,458,539 | 7/1984 | Bilstad et al. . |
| 4,481,827 | 11/1984 | Bilstad et al. . |
| 4,501,531 | 2/1985 | Bilstad et al. . |

(List continued on next page.)

FOREIGN PATENT DOCUMENTS 580 299 A1   7/1992   (EP) .

*Primary Examiner*—Joseph W. Drodge
(74) *Attorney, Agent, or Firm*—Daniel D. Ryan; Bradford R. L. Price; Amy L. H. Rockwell

(57) ABSTRACT

Blood processing systems and methods separate whole blood into red blood cells and a plasma constituent within a rotating centrifugal separation device. The systems and methods convey whole blood into the separation device through an inlet path including a pump operable at a prescribed rate. The systems and methods remove plasma constituent from the separation device through an outlet path including a pump operable at a prescribed rate. The systems and methods derive a value $H_b$ representing an apparent hematocrit of whole blood entering the separation device, where:

$$H_b = \frac{H_{rbc}(Q_b - Q_p)}{Q_b}$$

and where $H_{rbc}$ is a value relating to hematocrit of red blood cells in the separation device. The systems and methods generate outputs and control commands based, at least in part, upon $H_b$.

26 Claims, 8 Drawing Sheets

U.S. PATENT DOCUMENTS

| | | |
|---|---|---|
| 4,537,561 | 8/1985 | Xanthopoulos . |
| 4,540,406 | 9/1985 | Miles . |
| 4,573,961 | 3/1986 | King . |
| 4,648,866 | 3/1987 | Malbrancq et al. . |
| 4,655,742 | 4/1987 | Vantard . |
| 4,657,529 | 4/1987 | Prince et al. . |
| 4,692,138 | 9/1987 | Troutner et al. . |
| 4,708,714 | 11/1987 | Larsson et al. . |
| 4,713,176 | 12/1987 | Schoendorfer et al. . |
| 4,736,748 | 4/1988 | Nakamura et al. . |
| 4,769,001 | 9/1988 | Prince . |
| 4,795,314 | 1/1989 | Prybella et al. . |
| 4,850,995 | 7/1989 | Tie et al. . |
| 4,850,998 | 7/1989 | Schoendorfer . |
| 4,867,738 | 9/1989 | Mintz . |
| 4,879,040 | 11/1989 | Prince et al. . |
| 4,883,462 | 11/1989 | Williamson et al. . |
| 4,923,598 | 5/1990 | Schal . |
| 4,968,295 | 11/1990 | Neumann . |
| 4,994,188 | 2/1991 | Prince . |
| 4,995,268 | 2/1991 | Ash et al. . |
| 5,034,135 | 7/1991 | Fischel . |
| 5,069,792 | 12/1991 | Prince et al. . |
| 5,092,836 | 3/1992 | Polaschegg . |
| 5,112,298 | 5/1992 | Prince et al. . |
| 5,188,588 | 2/1993 | Schoendorfer et al. . |
| 5,234,608 | 8/1993 | Duff . |
| 5,298,171 | 3/1994 | Biesel . |
| 5,318,511 | 6/1994 | Riquier et al. . |
| 5,318,512 | 6/1994 | Neumann . |
| 5,370,802 | 12/1994 | Brown . |
| 5,378,227 | 1/1995 | O'Riordan et al. . |
| 5,421,812 | 6/1995 | Langley et al. . |
| 5,423,738 | 6/1995 | Robinson et al. . |
| 5,427,695 | 6/1995 | Brown . |
| 5,437,598 * | 8/1995 | Antwiler ................................. 494/1 |
| 5,437,624 | 8/1995 | Langley et al. . |
| 5,494,592 | 2/1996 | Latham, Jr. et al. . |
| 5,496,265 | 3/1996 | Langley et al. . |
| 5,730,883 | 3/1998 | Brown . |
| 6,059,979 * | 5/2000 | Brown ................................. 210/739 |

* cited by examiner

BLOOD PROCESSING SYSTEMS AND METHODS USING APPARENT HEMATOCRIT AS A PROCESS CONTROL PARAMETER

This application is a continuation of application Ser. No. 08/960,674 filed Oct. 30, 1997, now U.S. Pat. No. 6,059,979, which is a continuation of application Ser. No. 08/473,316 filed Jun. 7, 1995, now U.S. Pat. No. 5,730,883, which is a continuation-in-part of application Ser. No. 08/097,967, filed on Jul. 26, 1993, now abandoned, which is a continuation-in-part of U.S. application Ser. No. 07/965,088, filed on Oct. 22, 1992, now U.S. Pat. No. 5,370,802, which is a continuation-in-part of U.S. application Ser. No. 07/814,403, filed on Dec. 23, 1991, now abandoned.

FIELD OF THE INVENTION

The invention generally relates to blood processing systems and methods.

BACKGROUND OF THE INVENTION

Today people routinely separate whole blood by centrifugation into its various therapeutic components, such as red blood cells, platelets, and plasma.

Certain therapies transfuse large volumes of blood components. For example, some patients undergoing chemotherapy require the transfusion of large numbers of platelets on a routine basis. Manual blood bag systems simply are not an efficient way to collect these large numbers of platelets from individual donors.

On line blood separation systems are today used to collect large numbers of platelets to meet this demand. On line systems perform the separation steps necessary to separate concentration of platelets from whole blood in a sequential process with the donor present. On line systems establish a flow of whole blood from the donor, separate out the desired platelets from the flow, and return the remaining red blood cells and plasma to the donor, all in a sequential flow loop.

Large volumes of whole blood (for example, 2.0 liters) can be processed using an on line system. Due to the large processing volumes, large yields of concentrated platelets (for example, $4\times10^{11}$ platelets suspended in 200 ml of fluid) can be collected. Moreover, since the donor's red blood cells are returned, the donor can donate whole blood for on line processing much more frequently than donors for processing in multiple blood bag systems.

Nevertheless, a need still exists for further improved systems and methods for collecting cellular-rich concentrates from blood components in a way that lends itself to use in high volume, on line blood collection environments, where higher yields of critically needed cellular blood components like platelets can be realized.

As the operational and performance demands upon such fluid processing systems become more complex and sophisticated, the need exists for automated process controllers that can gather and generate more detailed information and control signals to aid the operator in maximizing processing and separation efficiencies.

SUMMARY OF THE INVENTION

The invention provides blood processing systems and methods that separate whole blood into red blood cells and a plasma constituent within a rotating centrifugal separation device. The systems and methods convey whole blood into the separation device through an inlet path including a pump operable at a prescribed rate. The systems and methods remove plasma constituent from the separation device through an outlet path including a pump operable at a prescribed rate.

According to the invention, the systems and methods derive a value $H_b$ representing an apparent hematocrit of whole blood entering the separation device, where:

$$H_b = \frac{H_{rbc}(Q_b - Q_p)}{Q_b}$$

and where $H_{rbc}$ is a value relating to hematocrit of red blood cells in the separation device.

In a preferred embodiment, the systems and methods generate a control command based, at least in part, upon $H_b$. In one implementation, the control command recirculates at least a portion of plasma constituent for mixing with whole blood conveyed into the separation device. In another implementation, the control command controls $Q_b$.

In a preferred embodiment, the systems and methods generate an output based, at least in part, upon $H_b$. In one implementation, the output comprises a value η representing efficiency of separation in the separation device, where:

$$\eta = \frac{Q_p}{(1-H_b)Q_b}$$

In a preferred embodiment, the value $H_{rbc}$ represents apparent hematocrit of red blood cells in the separation device, where:

$$H_{rbc} = 1 - \left(\frac{\beta}{gA\kappa S_Y}(q_b - q_p)\right)^{\frac{1}{k+1}}$$

where:

$q_b$ is inlet blood flow rate (cm³/sec), which when converted to ml/min, corresponds with $Q_b$, $q_p$ is measured plasma flow rate (in cm³/sec), which, when converted to ml/min corresponds with $Q_p$, β is a shear rate dependent term, and $S_Y$ is a red blood cell sedimentation coefficient (sec) and $\beta/S_Y = 15.8\times10^6$ sec⁻¹, A is the area of the separation device (cm²), g is the centrifugal acceleration (cm/sec²), which is the radius of the separation device multiplied by the rate of rotation squared $\Omega^2$ (rad/sec²), and k is a viscosity constant=0.625, and K is a viscosity constant based upon k and another viscosity constant α=4.5, where:

$$\kappa = \frac{k+2}{\alpha}\left[\frac{k+2}{k+1}\right]^{k+1} = 1.272$$

In a preferred embodiment, the systems and methods operate free of any a sensor to measure blood hematocrit either in the separation device or in the inlet path.

In a preferred embodiment, the systems and methods recirculate at least a portion of plasma constituent from the separation device at a prescribed rate $Q_{Recirc}$ for mixing with whole blood conveyed into the separation device. In this embodiment, the systems and methods control $Q_{Recirc}$ to achieve a desired hematocrit $H_i$ for whole blood conveyed into the separation device as follows:

$$Q_{Recirc} = \left[\frac{H_b}{H_i} - 1\right] \times Q_b$$

The various aspects of the invention are especially well suited for on line blood separation processes.

Other features and advantages of the invention will become apparent from the following description, the drawings, and the claims.

The various aspects of the invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
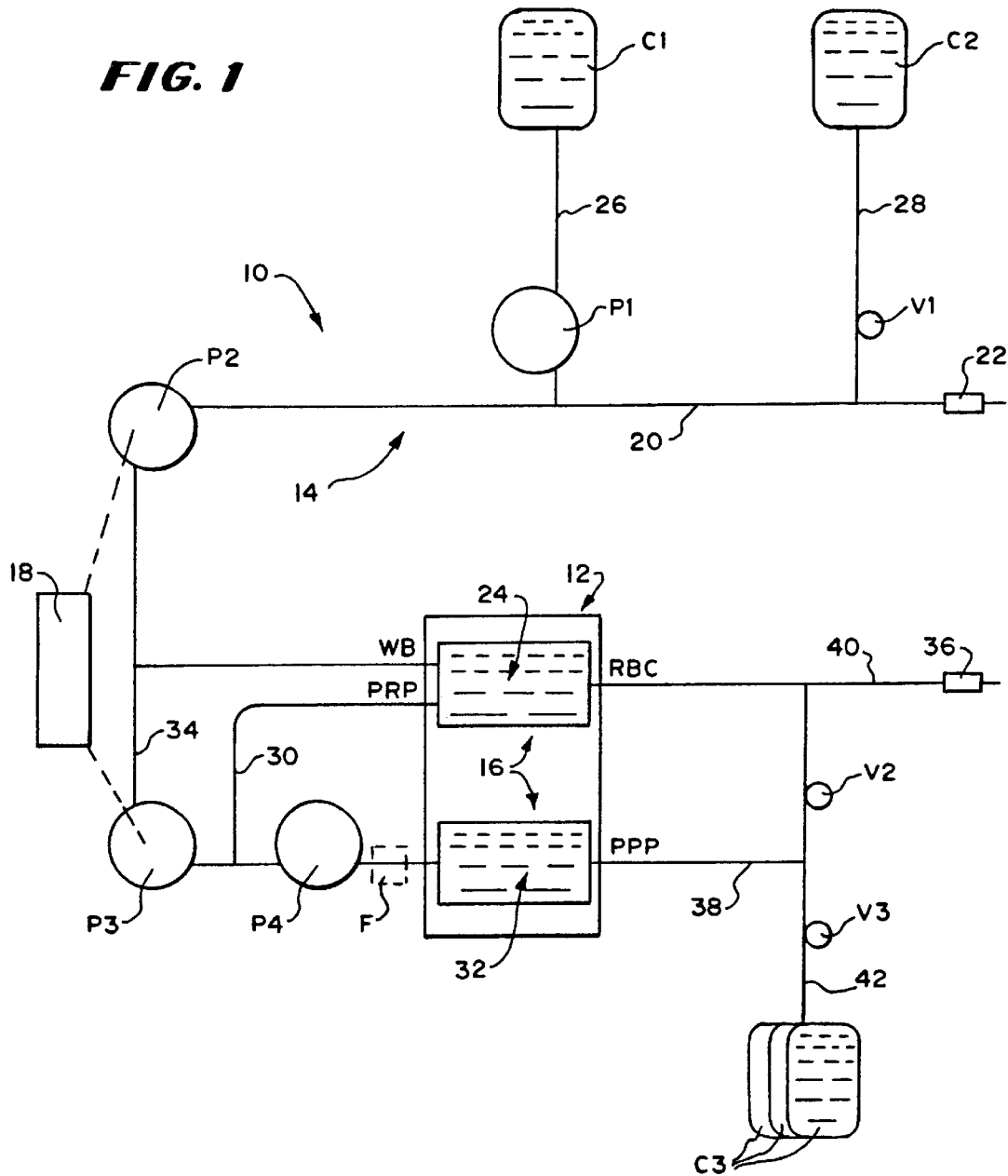
FIG. 1 is a diagrammatic view of a dual needle platelet collection system that includes a controller that embodies the features of the invention.

FIG. 1 shows in diagrammatic form an on line blood processing system 10 for carrying out an automated platelet collection procedure. The system 10 in many respects typifies a conventional two needle blood collection network, although a convention single needle network could also be used. The system 10 includes a processing controller 18 embodying the features of the invention.

I. The Separation system

The system 10 includes an arrangement of durable hardware elements, whose operation is governed by the processing controller 18. The hardware elements include a centrifuge 12, in which whole blood (WB) is separated into its various therapeutic components, like platelets, plasma, and red blood cells (RBC). The hardware elements will also include various pumps, which are typically peristaltic (designated P1 to P4); and various in line clamps and valves (designated V1 to V3). Of course, other types of hardware elements may typically be present, which FIG. 1 does not show, like solenoids, pressure monitors, and the like.

The system 10 typically also includes some form of a disposable fluid processing assembly 14 used in association with the hardware elements.

In the illustrated blood processing system 10, the assembly 14 includes a two stage processing chamber 16. In use, the centrifuge 12 rotates the processing chamber 16 to centrifugally separate blood components. A representative centrifuge that can be used is shown in Williamson et al U.S. Pat. No. 5,360,542, which is incorporated herein by reference.

The construction of the two stage processing chamber 16 can vary. For example, it can take the form of double bags, like the processing chambers shown in Cullis et al. U.S. Pat. No. 4,146,172. Alternatively, the processing chamber 16 can take the form of an elongated two stage integral bag, like that shown in Brown U.S. Pat. No. 5,370,802.

In the illustrated blood processing system 10, the processing assembly 14 also includes an array of flexible tubing that forms a fluid circuit. The fluid circuit conveys liquids to and from the processing chamber 16. The pumps P1–P4 and the valves V1–V3 engage the tubing to govern the fluid flow in prescribed ways. The fluid circuit further includes a number of containers (designated C1 to C3) to dispense and receive liquids during processing.

The controller 18 governs the operation of the various hardware elements to carry out one or more processing tasks using the assembly 14. The controller 18 also performs real time evaluation of processing conditions and outputs information to aid the operator in maximizing the separation and collection of blood components. The invention specifically concerns important attributes of the controller 18.

The system 10 can be configured to accomplish diverse types of blood separation processes. FIG. 1 shows the system 10 configured to carry out an automated two needle platelet collection procedure.

In a collection mode, a first tubing branch 20 and the whole blood inlet pump P2 direct WB from a draw needle 22 into the first stage 24 of the processing chamber 16.

Meanwhile, an auxiliary tubing branch 26 meters anticoagulant from the container C1 to the WB flow through the anticoagulant pump P1. While the type of anticoagulant can vary, the illustrated embodiment uses ACDA, which is a commonly used anticoagulant for pheresis.

The container C2 holds saline solution. Another auxiliary tubing branch 28 conveys the saline into the first tubing branch 20, via the in line valve V1, for use in priming and purging air from the system 10 before processing begins. Saline solution is also introduced again after processing ends to flush residual components from the assembly 14 for return to the donor.

Anticoagulated WB enters and fills the first stage 24 of the processing chamber 24. There, centrifugal forces generated during rotation of the centrifuge 12 separate WB into red blood cells (RBC) and platelet-rich plasma (PRP).

The PRP pump P4 operates to draw PRP from the first stage 24 of the processing chamber 16 into a second tubing branch 30 for transport to the second stage 32 of the processing chamber 16. There, the PRP is separated into platelet concentrate (PC) and platelet-poor plasma (PPP).

Optionally, the PRP can be conveyed through a filter F to remove leukocytes before separation in the second stage 32. The filter F can employ filter media containing fibers of the type disclosed in Nishimura et al U.S. Pat. No. 4,936,998, which is incorporated herein by reference. Filter media containing these fibers are commercially sold by Asahi Medical Company in filters under the trade name SEPA-CELL.

The system 10 includes a recirculation tubing branch 34 and an associated recirculation pump P3. The processing controller 18 operates the pump P3 to divert a portion of the PRP exiting the first stage 24 of the processing chamber 16 for remixing with the WB entering the first stage 24 of the processing chamber 16. The recirculation of PRP establishes desired conditions in the entry region of the first stage 24 to provide maximal separation of RBC and PRP.

As WB is drawn into the first chamber stage 24 for separation, the illustrated two needle system simultaneously returns RBC from the first chamber stage 24, along with a portion of the PPP from the second chamber stage 32, to the donor through a return needle 36 through tubing branches 38 and 40 and in line valve V2.

The system 10 also collects PC (resuspended in a volume of PPP) in some of the containers C3 through tubing branches 38 and 42 and in line valve V3 for storage and beneficial use. Preferable, the container(s) C3 intended to store the PC are made of materials that, when compared to DEHP-plasticized polyvinyl chloride materials, have greater gas permeability that is beneficial for platelet storage. For example, polyolefin material (as disclosed in Gajewski et al U.S. Pat. No. 4,140,162), or a polyvinyl chloride material plasticized with tri-2-ethylhexyl trimellitate (TEHTM) can be used.

The system 10 can also collect PPP in some of the containers C3 through the same fluid path. The continuous retention of PPP serves multiple purposes, both during and after the component separation process.

The retention of PPP serves a therapeutic purpose during processing. PPP contains most of the anticoagulant that is metered into WB during the component separation process. By retaining a portion of PPP instead of returning it all to the donor, the overall volume of anticoagulant received by the donor during processing is reduced. This reduction is particularly significant when large blood volumes are processed. The retention of PPP during processing also keeps the donor's circulating platelet count higher and more uniform during processing.

The system 10 can also derive processing benefits from the retained PPP.

The system 10 can, in an alternative recirculation mode, recirculate a portion of the retained PPP, instead of PRP, for mixing with WB entering the first compartment 24. Or, should WB flow be temporarily halted during processing, the system 10 can draw upon the retained volume of PPP as an anticoagulated "keep-open" fluid to keep fluid lines patent. In addition, at the end of the separation process, the system 10 draws upon the retained volume of PPP as a "rinse-back" fluid, to resuspend and purge RBC from the first stage compartment 24 for return to the donor through the return branch 40. After the separation process, the system 10 also operates in a resuspension mode to draw upon a portion of the retained PPP to resuspend PC in the second compartment 24 for transfer and storage in the collection container(s) C3.

II. The System Controller

The controller 18 carries out the overall process control and monitoring functions for the system 10 as just described.

In the illustrated and preferred embodiment (see FIG. 2), the controller comprises a main processing unit (MPU) 44. In the preferred embodiment, the MPU 44 comprises a type 68030 microprocessor made by Motorola Corporation, although other types of conventional microprocessors can be used.

In the preferred embodiment, the MPU 44 employs conventional real time multi-tasking to allocate MPU cycles to processing tasks. A periodic timer interrupt (for example, every 5 milliseconds) preempts the executing task and schedules another that is in a ready state for execution. If a reschedule is requested, the highest priority task in the ready state is scheduled. Otherwise, the next task on the list in the ready state is schedule.

A. Functional Hardware Control

The MPU 44 includes an application control manager 46. The application control manager 46 administers the activation of a library 48 of control applications (designated A1 to A3). Each control application A1–A3 prescribes procedures for carrying out given functional tasks using the system hardware (e.g., the centrifuge 12, the pumps P1–P4, and the valves V1–V3) in a predetermined way. In the illustrated and preferred embodiment, the applications A1–A3 reside as process software in EPROM's in the MPU 44.

The number of applications A1–A3 can vary. In the illustrated and preferred embodiment, the library 48 includes at least one clinical procedure application A1. The procedure application A1 contains the steps to carry out one prescribed clinical processing procedure. For the sake of example in the illustrated embodiment, the library 48 includes a procedure application A1 for carrying out the dual needle platelet collection process, as already generally described in connection with FIG. 1. Of course, additional procedure applications can be, and typically will be, included. For example, the library 48 can include a procedure application for carrying out a conventional single needle platelet collection process.

In the illustrated and preferred embodiment, the library 48 also includes a system optimization application A2. The system optimization application A2 contains interrelated, specialized utility functions that process information based upon real time processing conditions and empirical estimations to derive information and control variables that optimize system performance. Further details of the optimization application A2 will be described later.

The library 48 also includes a main menu application A3, which coordinates the selection of the various applications A1–A3 by the operator, as will also be described in greater detail later.

Of course, additional non-clinical procedure applications can be, and typically will be, included. For example, the library 48 can include a configuration application, which contains the procedures for allowing the operator to configure the default operating parameters of the system 10. As a further example, the library 48 can include a diagnostic application, which contains the procedures aiding service personnel in diagnosing and troubleshooting the functional integrity of the system, and a system restart application, which performs a full restart of the system, should the system become unable to manage or recover from an error condition.

An instrument manager 50 also resides as process software in EPROM's in the MPU 44. The instrument manager 50 communicates with the application control manager 46. The instrument manager 50 also communicates with low level peripheral controllers 52 for the pumps, solenoids, valves, and other functional hardware of the system.

Figure 2:
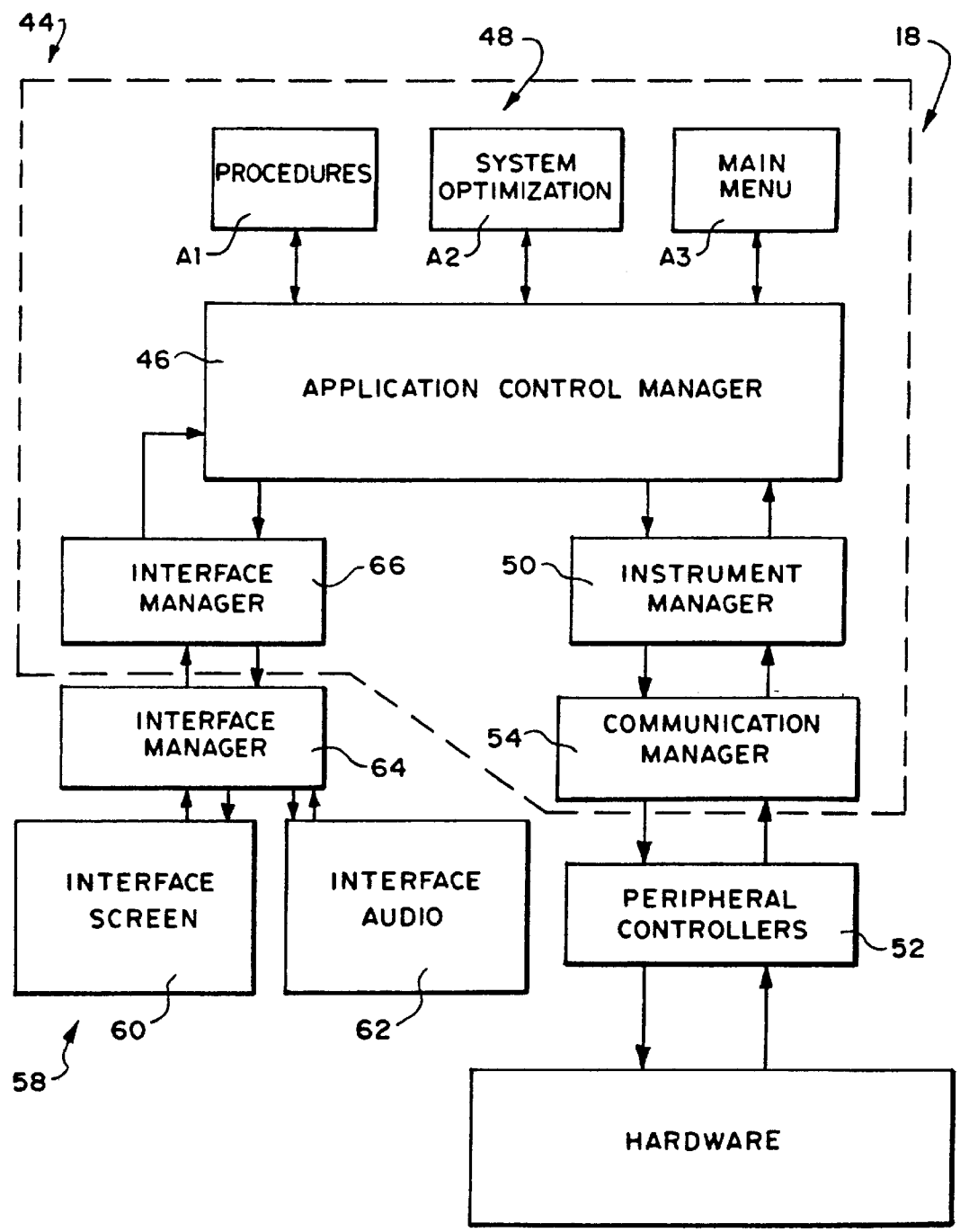
FIG. 2 is a diagrammatic flow chart view of the controller and associated system optimization application that embodies the features of the invention.

As FIG. 2 shows, the application control manager 46 sends specified function commands to the instrument manager 50, as called up by the activated application A1–A3. The instrument manager 50 identifies the peripheral controller or controllers 52 for performing the function and compiles hardware-specific commands. The peripheral controllers 52 communicate directly with the hardware to implement the hardware-specific commands, causing the hardware to operate in a specified way. A communication manager 54 manages low-level protocol and communications between the instrument manager 50 and the peripheral controllers 52.

As FIG. 2 also shows, the instrument manager 50 also conveys back to the application control manager 46 status data about the operational and functional conditions of the processing procedure. The status data is expressed in terms of, for example, fluid flow rates, sensed pressures, and fluid volumes measured.

The application control manager 46 transmits selected status data for display to the operator. The application control manager 46 transmits operational and functional conditions to the procedure application A1 and the performance monitoring application A2.

B. User Interface Control

In the illustrated embodiment, the MPU 44 also includes an interactive user interface 58. The interface 58 allows the operator to view and comprehend information regarding the operation of the system 10. The interface 58 also allows the operator to select applications residing in the application control manager 46, as well as to change certain functions and performance criteria of the system 10.

The interface 58 includes an interface screen 60 and, preferably, an audio device 62. The interface screen 60 displays information for viewing by the operator in alphanumeric format and as graphical images. The audio device 62 provides audible prompts either to gain the operator's attention or to acknowledge operator actions.

In the illustrated and preferred embodiment, the interface screen 60 also serves as an input device. It receives input from the operator by conventional touch activation. Alternatively or in combination with touch activation, a mouse or keyboard could be used as input devices.

An interface controller 64 communicates with the interface screen 60 and audio device 62. The interface controller 64, in turn, communicates with an interface manager 66, which in turn communicates with the application control manager 46. The interface controller 64 and the interface manager 66 reside as process software in EPROM's in the MPU 44.

Further details of the interface 58 are disclosed in copending application Serial No. xxx.

C. The System Optimization Application

Figure 3:
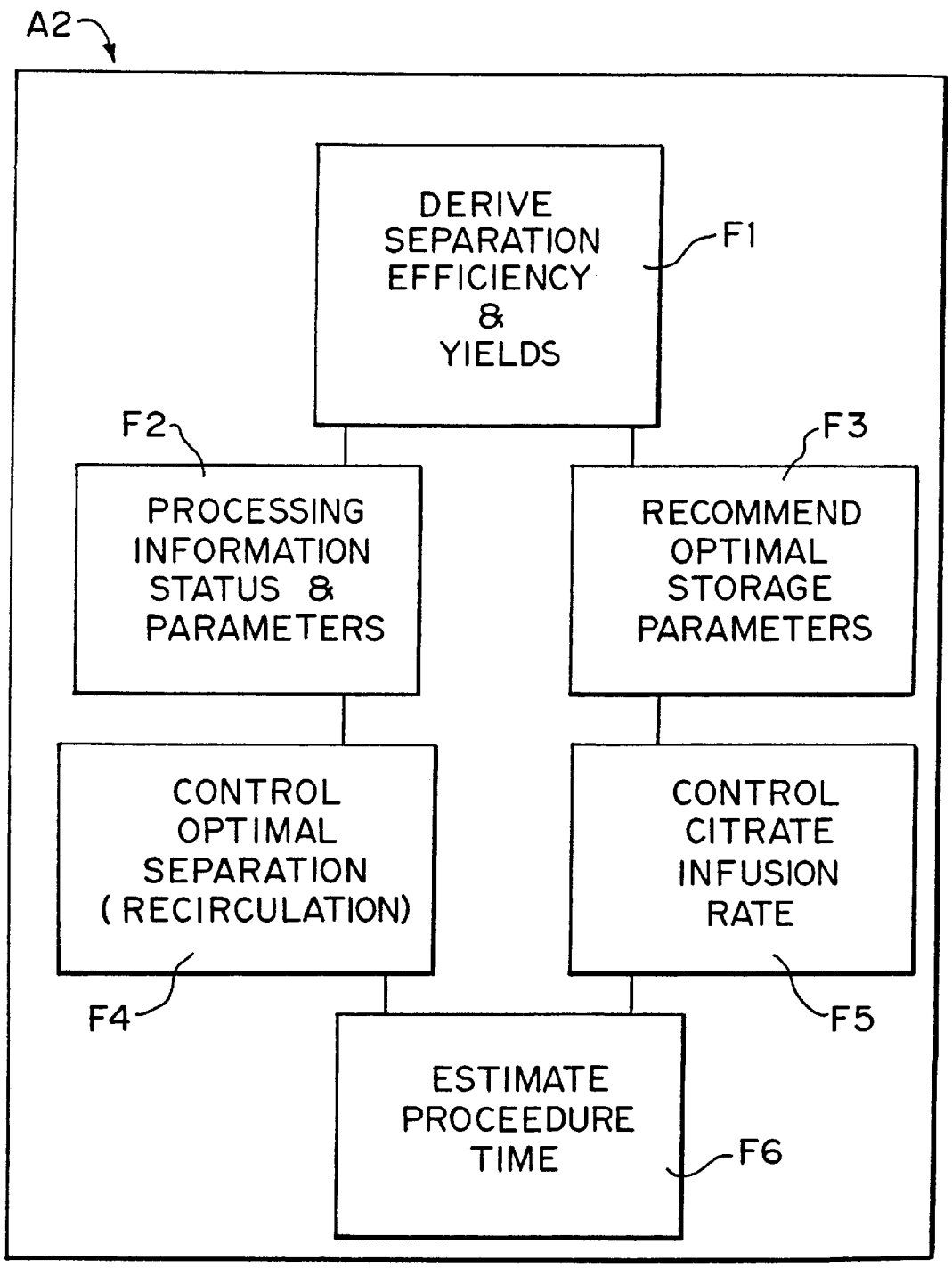
FIG. 3 is a diagrammatic view of the function utilities contained within the system optimization application shown in FIG. 2.

In the illustrated embodiment (as FIG. 3 shows), the system optimization application A2 contains six specialized yet interrelated utility functions, designated F1 to F6. Of course, the number and type of utility functions can vary.

In the illustrated embodiment, a utility function F1 derives the yield of the system 10 for the particular cellular component targeted for collection. For the platelet collection procedure application A1, the utility function F1 ascertains both the instantaneous physical condition of the system 10 in terms of its separation efficiencies and the instantaneous physiological condition of the donor in terms of the number of circulating platelets available for collection. From these, the utility function F1 derive the instantaneous yield of platelets continuously over the processing period.

Yet another utility function F2 relies upon the calculated platelet yield and other processing conditions to generate selected informational status values and parameters. These values and parameters are displayed on the interface 58 to aid the operator in establishing and maintaining optimal performance conditions. The status values and parameters derived by the utility function F2 can vary. For example, in the illustrated embodiment, the utility function F2 reports remaining volumes to be processed, remaining processing times, and the component collection volumes and rates.

Another utility function F3 calculates and recommends, based upon the platelet yield derived by the utility function F1, the optimal storage parameters for the platelets in terms of the number of storage containers and the volume amount of PPP storage media to use.

Other utility functions generate control variables based upon ongoing processing conditions for use by the applications control manager 46 to establish and maintain optimal processing conditions. For example, one utility function F4 generates control variables to optimize platelet separation conditions in the first stage 24. Another utility function F5 generates control variables to control the rate at which citrate anticoagulant is returned with the PPP to the donor to avoid potential citrate toxicity reactions.

Yet another utility function F6 derives an estimated procedure time, which predicts the collection time before the donor is connected.

Further details of these utility functions F1 to F6 will now be described in greater detail.

III. Deriving Platelet Yield

Figure 4:
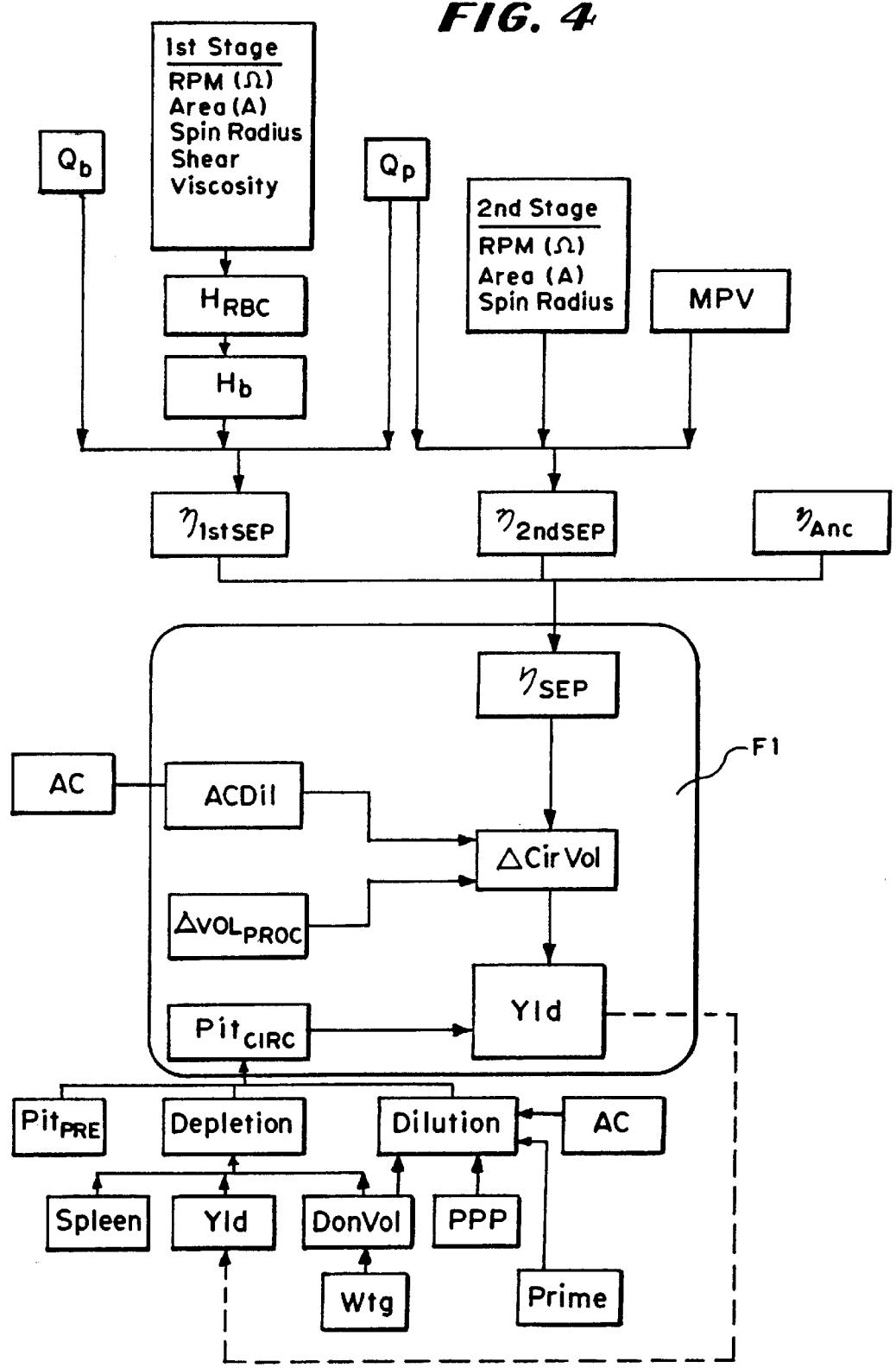
FIG. 4 is a diagrammatic flow chart view of the utility function contained within the system optimization application that derives the yield of platelets during a given processing session.

The utility function F1 (see FIG. 4) makes continuous calculations of the platelet separation efficiency ($\eta_{Plt}$) of the system 10. The utility function F1 treats the platelet separation efficiency $\eta_{Plt}$ as being the same as the ratio of plasma volume separated from the donor's whole blood relative to the total plasma volume available in the whole blood. The utility function F1 thereby assumes that every platelet in the plasma volume separated from the donor's whole blood will be harvested.

The donor's hematocrit changes due to anticoagulant dilution and plasma depletion effects during processing, so the separation efficiency $\eta_{Plt}$ does not remain at a constant value, but changes throughout the procedure. The utility function F1 contends with these process-dependent changes by monitoring yields incrementally. These yields, called incremental cleared volumes ($\Delta$ClrVol), are calculated by multiplying the current separation efficiency $\eta_{Plt}$ by the current incremental volume of donor whole blood, diluted with anticoagulant, being processed, as follows:

$$\Delta ClrVol = ACDil \times \eta_{Plt} \times \Delta VOL_{Proc} \quad \text{Eq (1)}$$

where:

$\Delta Vol_{Proc}$ is the incremental whole blood volume being processed, and

ACDil is an anticoagulant dilution factor for the incremental whole blood volume, computed as follows:

$$ACDil = \frac{AC}{AC+1} \quad \text{Eq (2)}$$

where:

AC is the selected ratio of whole blood volume to anticoagulant volume (for example 10:1 or "10"). AC may comprise a fixed value during the processing period. Alternatively, AC may be varied in a staged fashion according to prescribed criteria during the processing period.

For example, AC can be set at the outset of processing at a lesser ratio for a set initial period of time, and then increased in steps after subsequent time periods; for example, AC can be set at 6:1 for the first minute of processing, then raised to 8:1 for the next 2.5 to 3 minutes; and finally raised to the processing level of 10:1.

The introduction of anticoagulant can also staged by monitoring the inlet pressure of PRP entering the second processing stage 32. For example, AC can be set at 6:1 until the initial pressure (e.g. at 500 mmHg) falls to a set threshold level (e.g., 200 mmHg to 300 mmHg). AC can then be raised in steps up to the processing level of 10:1, while monitoring the pressure to assure it remains at the desired level.

The utility function F1 also makes continuous estimates of the donor's current circulating platelet count ($Plt_{Circ}$), expressed in terms of 1000 platelets per microliter ($\mu$l) of plasma volume (or k/$\mu$l). Like $\eta_{Plt}$, $Plt_{Circ}$ will change during processing due to the effects of dilution and depletion. The utility function F1 incrementally monitors the platelet yield in increments, too, by multiplying each incremental cleared plasma volume $\Delta$ClrVol (based upon an instantaneous calculation of $\eta_{Plt}$) by an instantaneous estimation of the circulating platelet count $Plt_{Cir}$. The product is an incremental platelet yield ($\Delta$yld), typically expressed as $e^n$ platelets, where $e^n = 0.5 \times 10^n$ platelets ($e^{11} = 0.5 \times 10^{11}$ platelets).

At any given time, the sum of the incremental platelet yields $\Delta$Yld constitutes the current platelet yield $Yld_{Current}$, which can also be expressed as follows:

$$Yld_{Current} = Yld_{Old} + \frac{\Delta ClrVol \times Plt_{Cur}}{100,000} \quad \text{Eq (3)}$$

where:

$Yld_{Old}$ is the last calculated $Yld_{Current}$, and $$\Delta Yld = \frac{\Delta ClrVol \times Plt_{Current}}{100,000} \quad \text{Eq (4)}$$

where:

$Plt_{Current}$ is the current (instantaneous) estimate of the circulating platelet count of the donor.

$\Delta$Yld is divided by 100,000 in Eq (4) to balance units.

The following provides further details in the derivation of the above-described processing variables by the utility function F1.

A. Deriving Overall Separation Efficiency $\eta_{Plt}$

The overall system efficiency $\eta_{Plt}$ is the product of the individual efficiencies of the parts of the system, as expressed as follows:

$$\eta_{Plt} = \eta_{1stSep} \times \eta_{2ndSep} \times \eta_{Anc} \quad \text{Eq (5)}$$

where:

$\eta_{1stSep}$ is the efficiency of the separation of PRP from WB in the first separation stage.

$\eta_{2ndSep}$ is the efficiency of separation PC from PRP in the second separation stage.

$\eta_{Anc}$ is the product of the efficiencies of other ancillary processing steps in the system.

1. First Stage Separation Efficiency $\eta_{1stSep}$

The utility function F1 (see FIG. 4) derives $\eta_{1stSep}$ continuously over the course of a procedure based upon measured and empirical processing values, using the following expression:

$$\eta_{Sep} = \frac{Q_p}{(1-H_b)Q_b} \quad \text{Eq (6)}$$

where:

$Q_b$ is the measured whole blood flow rate (in ml/min).

$Q_p$ is the measured PRP flow rate (in ml/min).

$H_b$ is the apparent hematocrit of the anticoagulated whole blood entering the first stage separation compartment. $H_b$ is a value derived by the utility based upon sensed flow conditions and theoretical considerations. The utility function F1 therefore requires no on-line hematocrit sensor to measure actual WB hematocrit.

The utility function F1 derives $H_b$ based upon the following relationship:

$$H_b = \frac{H_{rbc}(Q_b - Q_p)}{Q_b} \quad \text{Eq (7)}$$

where:

$H_{rbc}$ is the apparent hematocrit of the RBC bed within the first stage separation chamber, based upon sensed operating conditions and the physical dimensions of the first stage separation chamber. As with $H_b$, the utility function F1 requires no physical sensor to determine $H_{rbc}$, which is derived by the utility function according to the following expression:

$$H_{rbc} = 1 - \left(\frac{\beta}{gA\kappa S_Y}(q_b - q_p)\right)^{\frac{1}{k+1}} \quad \text{Eq (8)}$$

where:

$q_b$ is inlet blood flow rate (cm$^3$/sec), which is a known quantity which, when converted to ml/min, corresponds with $Q_b$ in Eq (6).

$q_p$ is measured PRP flow rate (in cm$^3$/sec), which is a known quantity which, when converted to ml/min corresponds with $Q_p$ in Eq (6).

$\beta$ is a shear rate dependent term, and $S_Y$ is the red blood cell sedimentation coefficient (sec). Based upon empirical data, Eq (8) assumes that $\beta/S_Y = 15.8 \times 10^6$ sec$^{-1}$.

A is the area of the separation chamber (cm$^2$), which is a known dimension.

g is the centrifugal acceleration (cm/sec$^2$), which is the radius of the first separation chamber (a known dimension) multiplied by the rate of rotation squared $\Omega^2$ (rad/sec$^2$) (another known quantity).

k is a viscosity constant=0.625, and K is a viscosity constant based upon k and another viscosity constant $\alpha$=4.5, where:

$$\kappa = \frac{k+2}{\alpha}\left[\frac{k+2}{k+1}\right]^{k+1} = 1.272 \quad \text{Eq (9)}$$

Eq (8) is derived from the relationships expressed in the following Eq (10):

$$H_{rbc}(1 - H_{rbc})^{(k+1)} = \frac{\beta H_b q_b}{gA\kappa S_Y} \quad \text{Eq (10)}$$

set forth in Brown, *The Physics of Continuous Flow Centrifugal Cell Separation*, "Artificial Organs" 1989; 13(1): 4–20)). Eq (8) solves Eq (10) for $H_{rbc}$.

2. The Second Stage Separation Efficiency $\eta_{2ndSep}$

The utility function F1 (see FIG. 4) also derives $\eta_{2ndSep}$ continuously over the course of a procedure based upon an algorithm, derived from computer modeling, that calculates what fraction of log-normally distributed platelets will be collected in the second separation stage 32 as a function of their size (mean platelet volume, or MPV), the flow rate ($Q_p$), area (A) of the separation stage 32, and centrifugal acceleration (g, which is the spin radius of the second stage multiplied by the rate of rotation squared $\Omega^2$).

Figure 8:
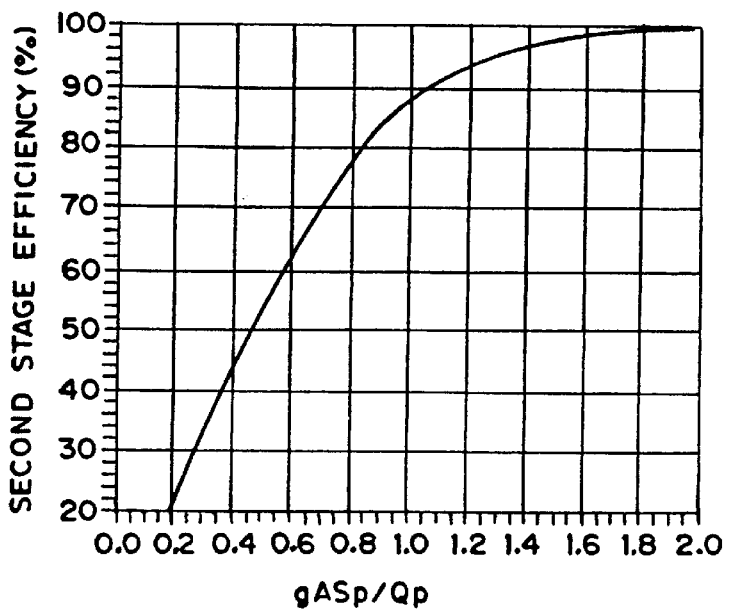
FIG. 8 is a graphical depiction of an algorithm used by the utility function shown in FIG. 4 expressing the relationship between the efficiency of platelet separation in the second stage chamber and a dimensionless parameter, which takes into account the size of the platelets, the plasma flow rate, the area of the chamber, and the speed of rotation.

The algorithm can be expressed in terms of a function shown graphically in FIG. 8. The graph plots $\eta_{2ndSep}$ in terms of a single dimensionless parameter $gAS_p/Q_p$, where:

$$S_p = 1.8 \times 10^{-9} MPV^{2/3} (\text{sec}),$$

and

MPV is the mean platelet volume (femtoliters, fl, or cubic microns), which can be measured by conventional techniques from a sample of the donor's blood collected before processing. There can be variations in MPV due to use of different counters. The utility function therefore may include a look up table to standardize MPV for use by the function according to the type of counter used. Alternatively, MPV can be estimated based upon a function derived from statistical evaluation of clinical platelet precount $Plt_{PRE}$ data, which the utility function can use. The inventor believes, based upon his evaluation of such clinical data, that the MPV function can be expressed as:

$$MPV(\text{fl}) \approx 11.5 - 0.009 Plt_{PRE}(k/\mu l)$$

3. Ancillary Separation Efficiencies $\eta_{Anc}$ $\eta_{Anc}$ takes into account the efficiency (in terms of platelet loss) of other portions of the processing system. $\eta_{Anc}$ takes into account the efficiency of transporting platelets (in PRP) from the first stage chamber to the second stage chamber; the efficiency of transporting platelets (also in PRP) through the leukocyte removal filter; the efficiency of resuspension and transferral of platelets (in PC) from the second stage chamber after processing; and the efficiency of reprocessing previously processed blood in either a single needle or a double needle configuration.

The efficiencies of these ancillary process steps can be assessed based upon clinical data or estimated based upon computer modeling. Based upon these considerations, a predicted value for $\eta_{Anc}$ can be assigned, which Eq (5) treats as constant over the course of a given procedure.

B. Deriving Donor Platelet Count ($Plt_{Circ}$)

The utility function F1 (see FIG. 4) relies upon a kinetic model to predict the donor's current circulating platelet count $Plt_{Circ}$ during processing. The model estimates the donor's blood volume, and then estimates the effects of dilution and depletion during processing, to derive $Plt_{Circ}$, according to the following relationships:

$$Plt_{Circ} = [(\text{Dilution}) \times Plt_{pre}] - (\text{Depletion}) \quad \text{Eq (11)}$$

where:

$Plt_{pre}$ is the donor's circulating platelet count before processing begins (k/$\mu$l), which can be measured by conventional techniques from a sample of whole blood taken from the donor before processing. There can be variations in $Plt_{pre}$ due to use of different counters (see, e.g., Peoples et al., "A Multi-Site Study of Variables Affecting Platelet Counting for Blood Component Quality Control," Transfusion (Special Abstract Supplement, 47th Annual Meeting), v. 34, No. 10S, October 1994 Supplement). The utility function therefore may include a look up table to standardize all platelet counts (such as, $Plt_{pre}$ and Pltpost, described later) for use by the function according to the type of counter used.

Dilution is a factor that reduces the donor's preprocessing circulating platelet count $Plt_{pre}$ due to increases in the donor's apparent circulating blood volume caused by the priming volume of the system and the delivery of anticoagulant. Dilution also takes into account the continuous removal of fluid from the vascular space by the kidneys during the procedure.

Depletion is a factor that takes into account the depletion of the donor's available circulating platelet pool by processing. Depletion also takes into account the counter mobilization of the spleen in restoring platelets into the circulating blood volume during processing.

1. Estimating Dilution

The utility function F1 estimates the dilution factor based upon the following expression:

$$Dilution = 1 - \frac{Prime + \frac{2ACD}{3} - PPP}{DonVol} \quad \text{Eq (12)}$$

where:
  Prime is the priming volume of the system (ml).
  ACD is the volume of anticoagulant used (current or end-point, depending upon the time the derivation is made)(ml).
  PPP is the volume of PPP collected (current or goal) (ml).
  DonVol (ml) is the donor's blood volume based upon models that take into account the donor's height, weight, and sex. These models are further simplified using empirical data to plot blood volume against donor weight linearized through regression to the following, more streamlined expression:

$$DonVol = 1024 + 51 Wgt (r^2 = 0.87) \quad \text{Eq (13)}$$

where:
  Wgt is the donor's weight (kg).

2. Estimating Depletion

The continuous collection of platelets depletes the available circulating platelet pool. A first order model predicts that the donor's platelet count is reduced by the platelet yield (Yld) (current or goal) divided by the donor's circulating blood volume (DonVol), expressed as follows:

$$Depl = \frac{100,000 \; Yld}{DonVol} \quad \text{Eq (14)}$$

where:
  Yld is the current instantaneous or goal platelet yield (k/$\mu$l). In Eq (14), Yld is multiplied by 100,000 to balance units.

Eq (14) does not take into account splenic mobilization of replacement platelets, which is called the splenic mobilization factor (or Spleen). Spleen indicates that donors with low platelets counts nevertheless have a large platelet reserve held in the spleen. During processing, as circulating platelets are withdrawn from the donor's blood, the spleen releases platelets it holds in reserve into the blood, thereby partially offsetting the drop in circulating platelets. The inventor has discovered that, even though platelet precounts vary over a wide range among donors, the total available platelet volume remains remarkably constant among donors. An average apparent donor volume is 3.10±0.25 ml of platelets per liter of blood. The coefficient of variation is 8.1%, only slightly higher than the coefficient of variation in hematocrit seen in normal donors.

The inventor has derived the mobilization factor Spleen from comparing actual measured depletion to Depl (Eq (14)), which is plotted and linearized as a function of $Plt_{Pre}$. Spleen (which is restricted to a lower limit of 1) is set forth as follows:

$$Spleen = [2.25 - 0.004 Plt_{Pre}] \geq 1 \quad \text{Eq (15)}$$

Based upon Eqs (14) and (15), the utility function derives Depletion as follows:

$$Depletion = \frac{100,000 \; Yld}{Spleen \times DonVol} \quad \text{Eq (16)}$$

C. Real Time Procedure Modifications

The operator will not always have a current platelet pre-count $Plt_{Pre}$ for every donor at the beginning of the procedure. The utility function F1 allows the system to launch under default parameters, or values from a previous procedure. The utility function F1 allows the actual platelet pre-count $Plt_{Pre}$, to be entered by the operator later during the procedure. The utility function F1 recalculates platelet yields determined under one set of conditions to reflect the newly entered values. The utility function F1 uses the current yield to calculate an effective cleared volume and then uses that volume to calculate the new current yield, preserving the platelet pre-count dependent nature of splenic mobilization.

The utility function F1 uses the current yield to calculate an effective cleared volume as follows:

$$lrVol = \frac{100,000 \times DonVol \times Yld_{Current}}{\left[DonVol - Prime - \frac{ACD}{3} + \frac{PPP}{2}\right] \times Pre_{Old} - \frac{50,000 \times Yld_{current}}{Spleen_{Old}}} \quad \text{Eq (17)}$$

where:
  ClrVol is the cleared plasma volume.
  DonVol is the donor's circulating blood volume, calculated according to Eq (13).
  $Yld_{Current}$ is the current platelet yield calculated according to Eq (3) based upon current processing conditions.
  Prime is the blood-side priming volume (ml).
  ACD is the volume of anticoagulant used (ml).
  PPP is the volume of platelet-poor plasma collected (ml).
  $Pre_{Old}$ is the donor's platelet count before processing entered before processing begun (k/$\mu$l).
  $Spleen_{Old}$ is the splenic mobilization factor calculated using Eq (16) based upon $Pre_{Old}$.
  The utility function F1 uses ClrVol calculated using Eq (17) to calculate the new current yield as follows:

$$Yld_{New} = \left[\frac{DonVol - Prime - \frac{ACD}{3} + \frac{PPP}{2}}{DonVol + \frac{ClrVol}{2 \times Spleen_{New}}}\right] \times \left[\frac{ClrVol \times Pre_{New}}{100,000}\right] \quad \text{Eq (18)}$$

where:
  $Pre_{New}$ is the revised donor platelet pre-count entered during processing (k/$\mu$l).
  $Yld_{New}$ is the new platelet yield that takes into account the revised donor platelet pre-count $Pre_{New}$.
  ClrVol is the cleared plasma volume, calculated according to Eq (17).

DonVol is the donor's circulating blood volume, calculated according to Eq (13), same as in Eq (17).

Prime is the blood-side priming volume (ml), same as in Eq (17).

ACD is the volume of anticoagulant used (ml), same as in Eq (17).

PPP is the volume of platelet-poor plasma collected (ml), same as in Eq (17).

$Spleen_{New}$ is the splenic mobilization factor calculated using Eq (15) based upon $Pre_{New}$.

IV. Deriving Other Processing Information

Figure 5:
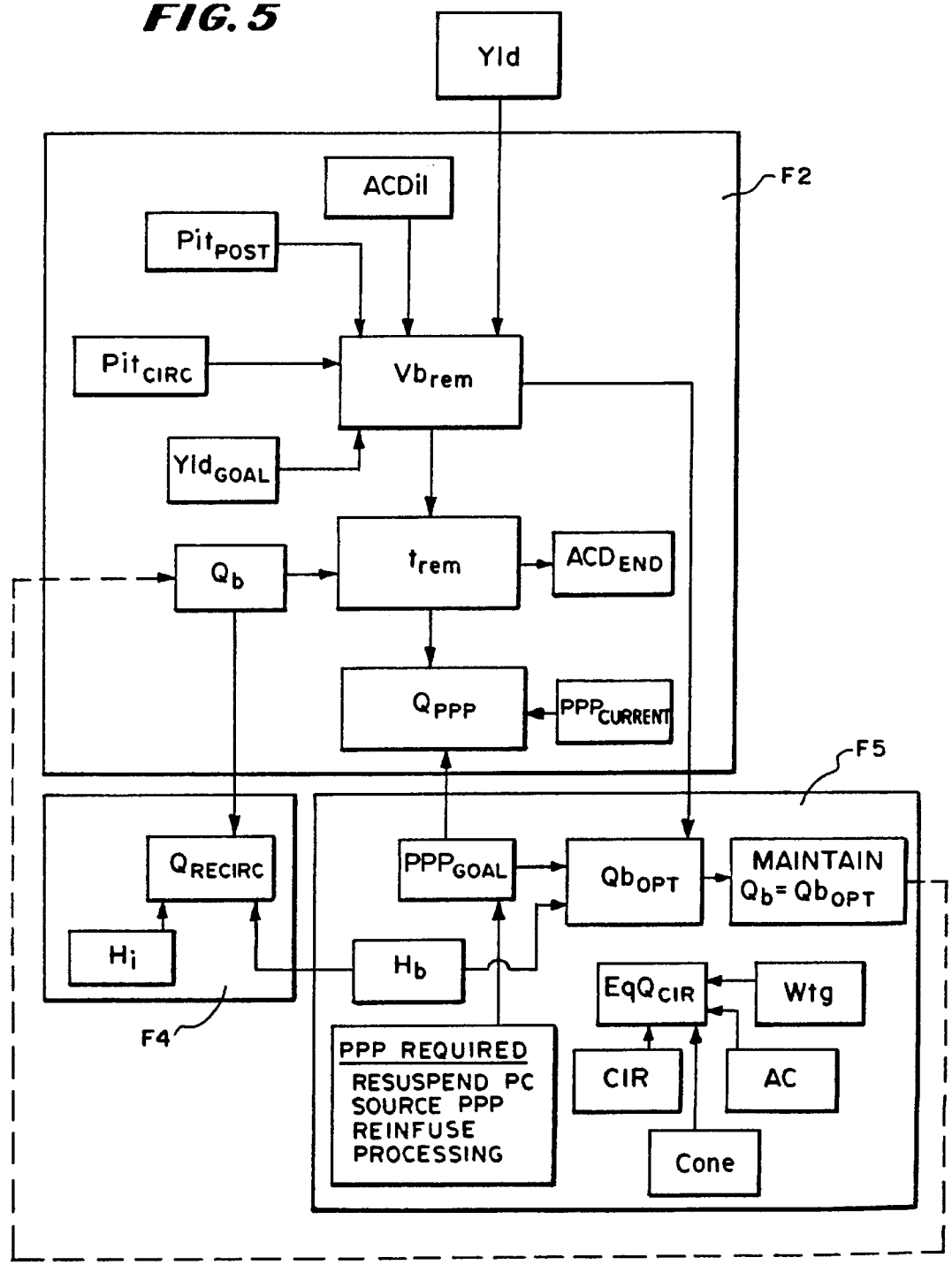
FIG. 5 is a diagrammatic flow chart view of the utility functions contained within the system optimization application that provide processing status and parameter information, generate control variables for achieving optimal separation efficiencies, and generate control variables that control the rate of citrate infusion during a given processing session.

The utility function F2 (see FIG. 5) relies upon the calculation of Yld by the first utility function F1 to derive other informational values and parameters to aid the operator in determining the optimum operating conditions for the procedure. The follow processing values exemplify derivations that the utility function F2 can provide.

A. Remaining Volume to be Processed

The utility function F2 calculates the additional processed volume needed to achieve a desired platelet yield $Vb_{rem}$ (in ml) by dividing the remaining yield to be collected by the expected average platelet count over the remainder of the procedure, with corrections to reflect the current operating efficiency $\eta_{Plt}$. The utility function F2 derives this value using the following expression:

$$Vb_{rem} = \frac{200,000 \times (Yld_{Goal} - Yld_{Current})}{\eta_{Plt} \times ACDil \times (Plt_{Current} + Plt_{Post})} \quad Eq(19)$$

where:

$Yld_{goal}$ is the desired platelet yield (k/μl), where:

$Vb_{rem}$ is the additional processing volume (ml) needed to achieve $Yld_{Goal}$.

$Yld_{Current}$ is the current platelet yield (k/μl), calculated using Eq (3) based upon current processing values.

$\eta_{Plt}$ is the present (instantaneous) platelet collection efficiency, calculated using Eq (5) based upon current processing values.

ACDil is the anticoagulant dilution factor (Eq (2)).

$Plt_{current}$ is the current (instantaneous) circulating donor platelet count, calculated using Eq (11) based upon current processing values.

$Plt_{Post}$ is the expected donor platelet count after processing, also calculated using Eq (11) based upon total processing values.

B. Remaining Procedure Time

The utility function F2 also calculates remaining collection time ($t_{rem}$) (in min) as follows:

$$t_{rem} = \frac{Vb_{rem}}{Q_b} \quad Eq(20)$$

where:

$Vb_{rem}$ is the remaining volume to be processed, calculated using Eq (19) based upon current processing conditions.

$Q^b$ is the whole blood flow rate, which is either set by the user or calculated as $Q^b_{Opt}$ using Eq (31), as will be described later.

C. Plasma Collection

The utility function F2 adds the various plasma collection requirements to derive the plasma collection volume ($PPP_{Goal}$) (in ml) as follows:

$$PPP_{Goal} = PPP_{PC} + PPP_{Source} + PPP_{Reinfuse} + PPP_{Waste} + PPP_{CollCham} \quad Eq(21)$$

where:

$PPP_{PC}$ is the platelet-poor plasma volume selected for the PC product, which can have a typical default value of 250 ml, or be calculated as an optimal value $Plt_{Med}$ according to Eq (28), as will be described later.

$PPP_{Source}$ is the platelet-poor plasma volume selected for collection as source plasma.

$PPP_{Waste}$ is the platelet-poor plasma volume selected to be held in reserve for various processing purposes (Default=30 ml).

$PPP_{CollCham}$ is the volume of the plasma collection chamber (Default=40 ml).

$PPP_{Reinfuse}$ is the platelet-poor plasma volume that will be reinfusion during processing.

D. Plasma Collection Rate

The utility function F2 calculates the plasma collection rate ($Q_{PPP}$) (in ml/min) as follows:

$$Q_{PPP} = \frac{PPP_{Goal} - PPP_{Current}}{t_{rem}} \quad Eq(22)$$

where:

$PPP_{Goal}$ is the desired platelet-poor plasma collection volume (ml).

$PPP_{Current}$ is the current volume of platelet-poor plasma collected (ml).

$t_{rem}$ is the time remaining in collection, calculated using Eq (20) based upon current processing conditions.

E. Total Anticipated AC Usage

The utility function F2 can also calculate the total volume of anticoagulant expected to be used during processing ($ACD_{End}$) (in ml) as follows:

$$ACD_{End} = ACD_{Current} + \frac{Q_b \times t_{rem}}{1 + AC} \quad Eq(23)$$

where:

$ACD_{Current}$ is the current volume of anticoagulant used (ml).

AC is the selected anticoagulant ratio, $Q_b$ is the whole blood flow rate, which is either set by the user or calculated using Eq (31) as $Q^b_{Opt}$ based upon current processing conditions.

$t_{rem}$ is the time remaining in collection, calculated using Eq (20) based upon current processing conditions.

V. Recommending optimum Platelet Storage Parameters

Figure 6:
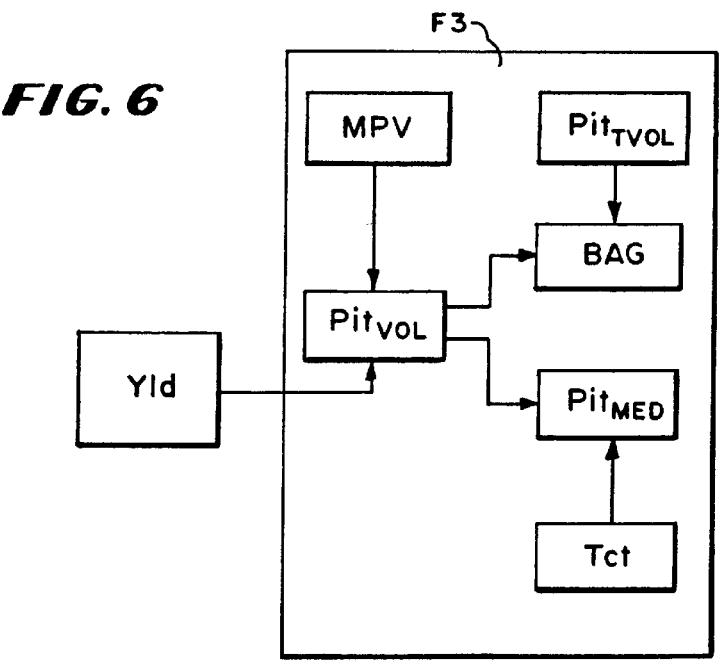
FIG. 6 is a diagrammatic flow chart view of the utility function contained within the system optimization application that recommends optimal storage parameters based upon the yield of platelets during a given processing session.

The utility function F3 (see FIG. 6) relies upon the calculation of Yld by the utility function F1 to aid the operator in determining the optimum storage conditions for the platelets collected during processing.

The utility function F3 derives the optimum storage conditions to sustain the platelets during the expected storage period in terms of the number of preselected storage containers required for the platelets $Plt_{Bag}$ and the volume of plasma (PPP) $Plt_{Med}$ (in ml) to reside as a storage medium with the platelets.

The optimal storage conditions for platelets depends upon the volume being stored $Plt_{Vol}$, expressed as follows:

$$Plt_{Vol} = Yld \times MPV \qquad Eq\,(24)$$

where:

Yld is the number of platelets collected, and

MPV is the mean platelet volume.

As $Plt_{Vol}$ increases, so too does the platelets' demand for oxygen during the storage period. As $Plt_{Vol}$ increases, the platelets' glucose consumption to support metabolism and the generation of carbon dioxide and lactate as a result of metabolism also increase. The physical characteristics of the storage containers in terms of surface area, thickness, and material are selected to provide a desired degree of gas permeability to allow oxygen to enter and carbon dioxide to escape the container during the storage period.

The plasma storage medium contains bicarbonate $HCO_3$, which buffers the lactate generated by platelet metabolism, keeping the pH at a level to sustain platelet viability. As $Plt_{Vol}$ increases, the demand for the buffer effect of $HCO_3$, and thus more plasma volume during storage, also increases.

A. Deriving $Plt_{Bag}$

Figure 9:
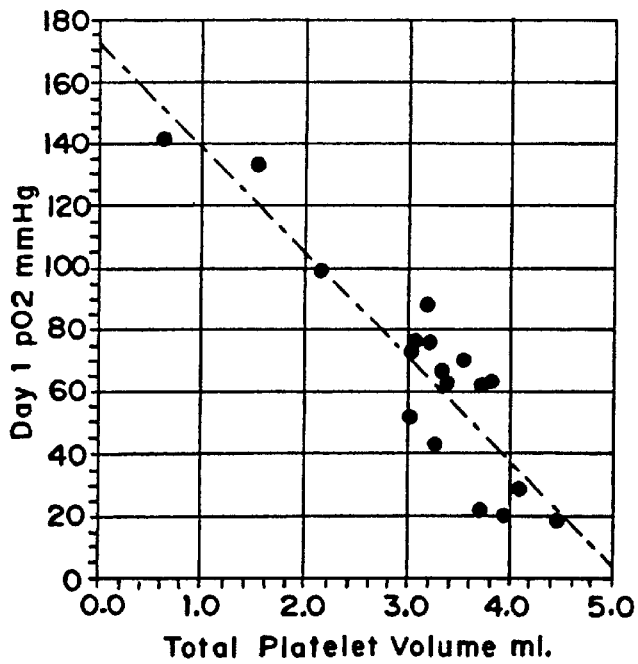
FIG. 9 is a graph showing the relationship between the partial pressure of oxygen and the permeation of a particular storage container, which the utility function shown in FIG. 6 takes into account in recommending optimal storage parameters in terms of the number of storage containers.

The partial pressure of oxygen $pO_2$ (mmHg) of platelets stored within a storage container having a given permeation decreases in relation to the total platelet volume $Plt_{Vol}$ the container holds. FIG. 9 is a graph based upon test data showing the relationship between $pO_2$ measured after one day of storage for a storage container of given permeation. The storage container upon which FIG. 9 is based has a surface area of 54.458 in² and a capacity of 1000 ml. The storage container has a permeability to $O_2$ of 194 cc/100 in²/day, and a permeability to $CO_2$ 1282 cc/100 in²/day.

When the partial pressure $pO_2$ drops below 20 mmHg, platelets are observed to become anaerobic, and the volume of lactate byproduct increases significantly. FIG. 9 shows that the selected storage container can maintain $pO_2$ of 40 mmHg (well above the aerobic region) at $Plt_{Vol} \leq 4.0$ ml. On this conservative basis, the 4.0 ml volume is selected as the target volume $Plt_{TVol}$ for this container. Target volumes $Plt_{TVol}$ for other containers can be determined using this same methodology.

The utility function F3 uses the target platelet volume $Plt_{TVol}$ to compute $Plt_{Bag}$ as follows:

$$BAG = \frac{Plt_{Vol}}{Plt_{TVol}} \qquad Eq\,(25)$$

and:

$Plt_{Bag}=1$ when $BAG \leq 1.0$, otherwise $Plt_{Bag}=[BAG+1]$, where $[BAG+1]$ is the integer part of the quantity BAG+1.

For example, given a donor MPV of 9.5 fl, and a Yld of $4 \times 10^{11}$ platelets ($Plt_{Vol}=3.8$ ml), and given $Plt_{TVol}=4.0$ ml, BAG=0.95, and $Plt_{Bag}=1$. If the donor MPV is 11.0 fl and the yield Yld and $Plt_{TVol}$ remain the same ($Plt_{Vol}=4.4$ ml), BAG=1.1 and $Plt_{Bag}=2$.

When $Plt_{Bag}>1$, $Plt_{Vol}$ is divided equally among the number of containers called for.

B. Deriving $Plt_{Med}$

The amount of bicarbonate used each day is a function of the storage thrombocytocrit Tct (%), which can be expressed as follows:

$$Tct = \frac{Plt_{Vol}}{Plt_{Med}} \qquad Eq\,(26)$$

Figure 10:
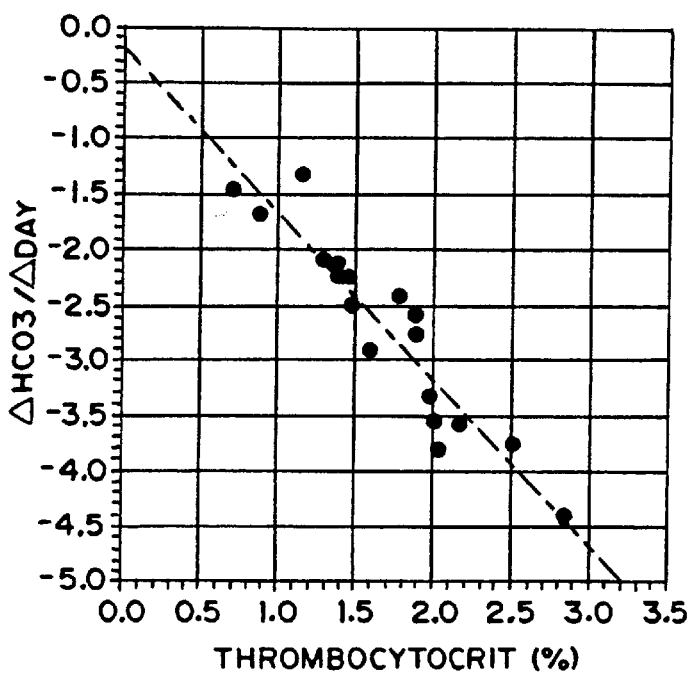
FIG. 10 is a graph showing the relationship between the consumption of bicarbonate and storage thrombocytocrit for a particular storage container, which the utility function shown in FIG. 6 takes into account in recommending optimal storage parameters I n terms of the volume of plasma storage medium.

The relationship between bicarbonate $HCO_3$ consumption per day and Tct can be empirically determined for the selected storage container. FIG. 10 shows a graph showing this relationship for the same container that the graph in FIG. 9 is based upon. The y-axis in FIG. 10 shows the empirically measured consumption of bicarbonate per day (in Meq/L) based upon Tct for that container. The utility function F3 includes the data expressed in FIG. 10 in a look-up table.

The utility function F3 derives the anticipated decay of bicarbonate per day over the storage period $\Delta HCO_3$ as follows:

$$\Delta HCO_3 = \frac{Don_{HCO_3}}{Stor} \qquad Eq\,(27)$$

where:

$Don_{HCO_3}$ is the measured bicarbonate level in the donor's blood (Meq/L), or alternatively, is the bicarbonate level for a typical donor, which is believed to be 19.0 Meq/L±1.3, and Stor is the desired storage interval (in days, typically between 3 to 6 days).

Given $\Delta HCO_3$, the utility function F3 derives Tct from the look up table for selected storage container. For the storage container upon which FIG. 10 is based, a Tct of about 1.35 to 1.5% is believed to be conservatively appropriate in most instances for a six day storage interval.

Knowing Tct and $Plt_{Vol}$, the utility function F3 computes $Plt_{Med}$ based upon Eq (25), as follows:

$$Plt_{Med} = \frac{Plt_{Vol}}{\frac{Tct}{100}} \qquad Eq\,(28)$$

When $Plt_{Bag}>1$, $Plt_{Med}$ is divided equally among the number of containers called for. $PPP_{PC}$ is set to $Plt_{Med}$ in Eq (21).

VI. Deriving Control Variables

The utility functions F4 and F5 rely upon the above-described matrix of physical and physiological relationships to derive process control variables, which the application control manager 46 uses to optimize system performance. The follow control variables exemplify derivations that the utility functions F4 and F5 can provide for this purpose.

A. Promoting High Platelet Separation Efficiencies By Recirculation

A high mean platelet value MPV for collected platelets is desirable, as it denotes a high separation efficiency for the first separation stage and the system overall. Most platelets average about 8 to 10 femtoliters, as measured by the Sysmex K-1000 machine (the smallest of red blood cells begin at about 30 femtoliters). The remaining minority of the platelet population constitutes platelets that are physically larger. These larger platelets typically occupy over $15 \times 10^{-15}$ liter per platelet, and some are larger than 30 femtoliters.

These larger platelets settle upon the RBC interface in the first separation chamber quicker than most platelets. These larger platelets are most likely to become entrapped in the RBC interface and not enter the PRP for collection. Efficient separation of platelets in the first separation chamber lifts the larger platelets from the interface for collection in the PRP. This, in turn, results a greater population of larger platelets in the PRP, and therefore a higher MPV.

Figure 11:
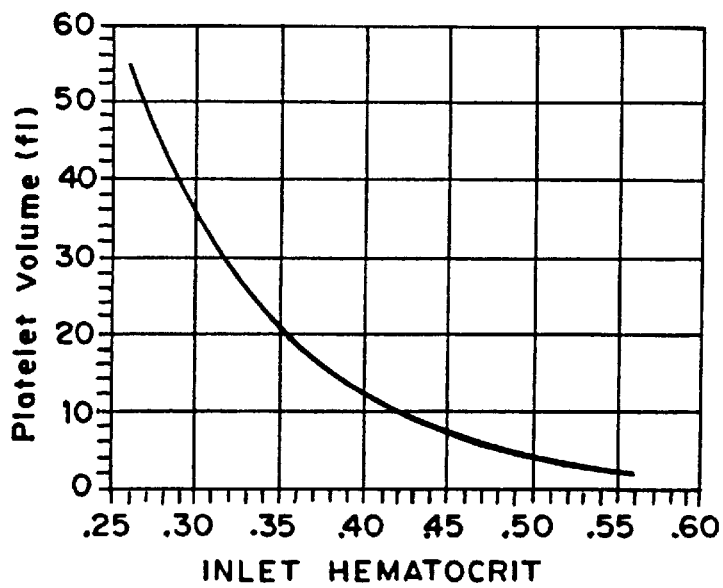
FIG. 11 is a graph showing the efficiency of platelet separation, expressed in terms of mean platelet volume, in terms of inlet hematocrit, which a utility function shown in FIG. 5 takes into account in generating a control variable governing plasma recirculation during processing.

FIG. 11, derived from clinical data, shows that the efficiency of platelet separation, expressed in terms of MPV, is highly dependent upon the inlet hematocrit of WB entering the first stage processing chamber. This is especially true at hematocrits of 30% and below, where significant increases in separation efficiencies can be obtained.

Based upon this consideration, the utility function F4 sets a rate for recirculating PRP back to the inlet of the first separation stage $Q_{Recirc}$ to achieve a desired inlet hematocrit $H_i$ selected to achieve a high MPV. The utility function F4 selects $H_i$ based upon the following red cell balance equation:

$$Q_{Recirc} = \left[\frac{H_b}{H_i} - 1\right] \times Q_b \qquad \text{Eq (29)}$$

In a preferred implementation, $H_i$ is no greater that about 40%, and, most preferably, is about 32%.

B. Citrate Infusion Rate

Citrate in the anticoagulant is rapidly metabolized by the body, thus allowing its continuous infusion in returned PPP during processing. However, at some level of citrate infusion, donors will experience citrate toxicity. These reactions vary in both strength and nature, and different donors have different threshold levels. A nominal a-symptomatic citrate infusion rate (CIR), based upon empirical data, is believed to about 1.25 mg/kg/min. This is based upon empirical data that shows virtually all donors can tolerate apheresis comfortably at an anticoagulated blood flow rates of 45 ml/min with an anticoagulant (ACD-A anticoagulant) ratio of 10:1.

Taking into account that citrate does not enter the red cells, the amount given to the donor can be reduced by continuously collecting some fraction of the plasma throughout the procedure, which the system accomplishes. By doing so, the donor can be run at a higher flow rate than would be expected otherwise. The maximum a-symptomatic equivalent blood flow rate ($EqQ^b_{CIR}$) (in ml/min) under these conditions is believed to be:

$$EqQb_{CIR} = \frac{CIR \times (AC + 1) \times Wgt}{Citrate\ Conc} \qquad \text{Eq (30)}$$

where:

CIR is the selected nominal a-symptomatic citrate infusion rate, or 1.25 mg/kg/min.

AC is the selected anticoagulant ratio, or 10:1.

Wgt is the donor's weight (kg).

CitrateConc is the citrate concentration in the selected anticoagulant, which is 21.4 mg/ml for ACD-A anticoagulant.

C. Optimum Anticoagulated Blood Flow

The remaining volume of plasma that will be returned to the donor is equal to the total amount available reduced by the amount still to be collected. This ratio is used by the utility function F5 (see FIG. 5) to determine the maximum, or optimum, a-symptomatic blood flow rate ($Q^b_{Opt}$) (in ml/min) that can be drawn from the donor, as follows:

$$Qb_{Opt} = \frac{(1 - H_b) \times Vb_{rem}}{(1 - H_b) \times Vb_{rem} - (PPP_{Goal} - PPP_{Current})} \times EqQb_{CIR} \qquad \text{Eq (31)}$$

where:

$H_b$ is the anticoagulated hematocrit, calculated using Eq (7) based upon current processing conditions.

$Vb_{Rem}$ is the remaining volume to be processed, calculated using Eq (19) based upon current processing conditions.

$EqQ^B_{CIR}$ is the citrate equivalent blood flow rate, calculated using Eq (30) based upon current processing conditions.

$PPP_{Goal}$ is the total plasma volume to be collected (ml).

$PPP_{Current}$ is the current plasma volume collected (ml).

VII. Estimated Procedure Time

Figure 7:
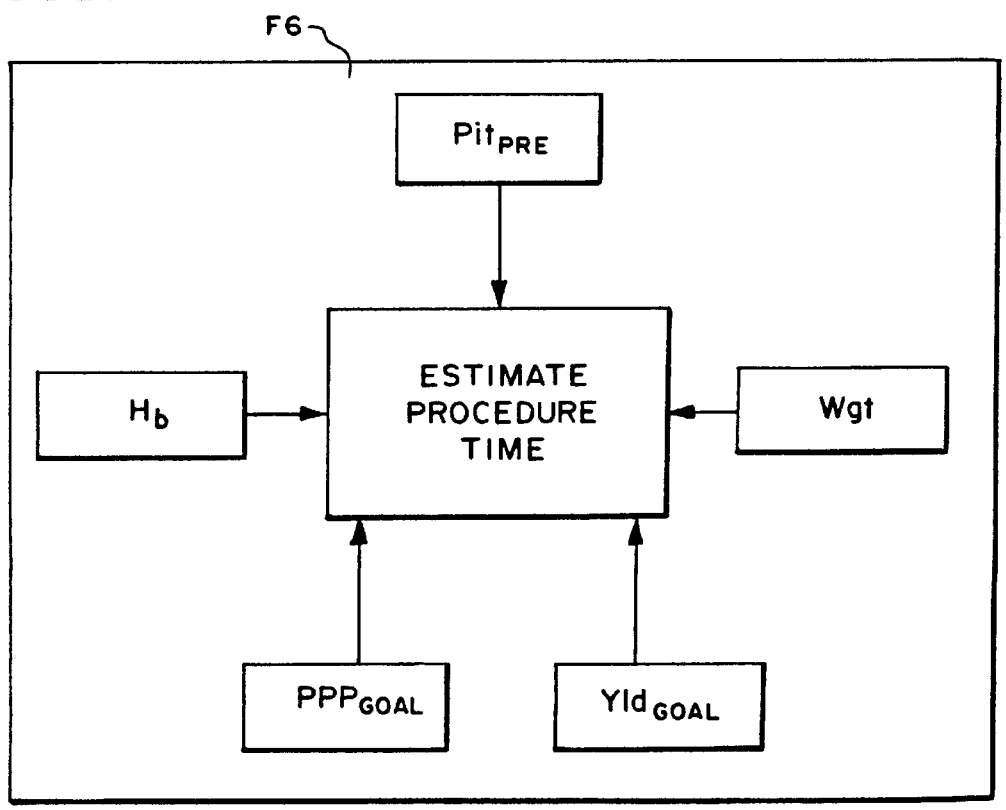
FIG. 7 is a diagrammatic flow chart view of the utility function contained within the system optimization application that estimates the processing time before commencing a given processing session.

The utility function F6 (see FIG. 7) derives an estimated procedure time (t) (in min), which predicts the collection time before the donor is connected. To derive the estimated procedure time t, the utility function F6 requires the operator to input the desired yield $Yld_{Goal}$ and desired plasma collection volume $PPP_{Goal}$, and further requires the donor weight Wgt, platelet pre-count $Plt_{Pre}$, and hematocrit $H_b$ or a default estimate of it. If the operator wants recommended platelet storage parameters, the utility function requires MPV as an input.

The utility function F6 derives the estimated procedure time t as follows:

$$t = \frac{-b + \sqrt{b^2 - 4ac}}{2a} \qquad \text{Eq (32)}$$

where:

$$a = \frac{H_{eq} - H_b}{(1 - H_b)} EqQb_{CIR} \qquad \text{Eq (33)}$$

$$b = \frac{(H_{eq} - H_b - \lambda H_b EqQb_{CIR})PPP}{(1 - H_b)^2} - H_{Eq}PV \qquad \text{Eq (34)}$$

$$c = \left[PV - \frac{PPP}{(1 - H_b)^2}\right]\lambda H_b \frac{PPP}{(1 - H_b)} \qquad \text{Eq (35)}$$

and where:

$H_{eq}$ is a linearized expression of the RBC hematocrit $H_{RBC}$, as follows:

$$H_{eq} = 0.9489 - \lambda H_b EqQ^b_{CIR} \qquad \text{Eq (36)}$$

where:

$H_b$ is the donor's anticoagulated hematocrit, actual or default estimation.

$EqQ^b_{CIR}$ is the maximum a-symptomatic equivalent blood flow rate calculated according to Eq (30).

and $$\lambda = \frac{61,463}{\Omega^2} \quad \text{Eq (37)}$$

where:
$\Omega$ is the rotation speed of the processing chamber (rpm).
and where:
PPP is the desired volume of plasma to be collected (ml).
PV is the partial processed volume, which is that volume that would need to be processed if the overall separation efficiency $\eta_{Plt}$ was 100%, derived as follows:

$$PV = \frac{ClrVol}{\eta_{Anc} \times \eta_{2ndSep} \times ACDil} \quad \text{Eq (38)}$$

where:
ACDil is the anticoagulant dilution factor (Eq (2)).
ClrVol is the cleared volume, derived as:

$$ClrVol = \frac{100,000 \times DonVol \times Yld}{\left[DonVol - Prime - \frac{ACD_{Est}}{3} + \frac{PPP}{2}\right] \times Plt_{Pre} - \frac{50,000 \times Yld}{Spleen}}$$

where:
Yld is the desired platelet yield.
DonVol is the donor's blood volume=1024+51Wgt (ml).
Prime is the blood side priming volume of the system (ml).
$ACD_{Est}$ is the estimated anticoagulant volume to be used (ml).
$Plt_{Pre}$ is the donor's platelet count before processing, or a default estimation of it.
Spleen is the is the splenic mobilization factor calculated using Eq (16) based upon $Plt_{Pre}$.
The function F6 also derives the volume of whole blood needed to be processed to obtain the desired $Yld_{Goal}$. This processing volume, WBVol, is expressed as follows:

$$WBVol = t \times EqQb_{CIR} \times \frac{PPP_{Goal}}{(1 - H_b)} + WB_{RES}$$

where:
t is the estimated procedure time derived according to Eq(32).
$H_b$ is the donor's anticoagulated hematocrit, actual or default estimation.
$EqQ^b_{CIR}$ is the maximum a-symptomatic equivalent blood flow rate calculated according to Eq (30).
$PPP_{GOAL}$ is the desired plasma collection volume.
$WB_{RES}$ is the residual volume of whole blood left in the system after processing, which is a known system variable and depends upon the priming volume of the system.
Various features of the inventions are set forth in the following claims.

I claim:

1. A blood processing system comprising
a centrifugal separation device rotatable about a rotational axis at a controlled rate of rotation, the separation device having an area A,
an inlet path operable to convey whole blood at a determinable rate $Q_b$ into the separation device for separation into red blood cells and a plasma constituent, the whole blood in the inlet path having an actual whole blood hematocrit value, the red blood cells in the separation device having an actual red blood cell hematocrit value,
an outlet path operable to remove plasma constituent from the separation device at a determinable rate $Q_p$ at least in part while whole blood is conveyed into the separation device,
an outlet path operable to remove red blood cells from the separation device at least in part while whole blood is conveyed into the separation device and plasma is removed from the separation device,
a controller including a stage operable, at least in part while whole blood is conveyed into the separation device and plasma and red blood cells are removed from the separation device, to derive a value $H_b$ representing an apparent hematocrit of whole blood entering the separation device and a value $H_{rbc}$ representing Eq (39)

an apparent hematocrit of red blood cells within the separation device, where:

$$H_b = f(H_{rbc})$$

and where:

$$H_{rbc} = f(Q_b, Q_p, A, g, RBC)$$

where:
g represents a centrifugal acceleration factor based upon the controlled rate of rotation, and
RBC represents at least one red blood cell dependent factor not including either the actual whole blood hematocrit value or the actual red blood cell hematocrit value, and
the controller including a stage operable to generate a control command at least in part while whole blood is conveyed into the separation device and plasma and red blood cells are removed from the separation device, based, at least in part, upon $H_b$.

2. A system according to claim 1
wherein, the controller derives $H_b$ based upon a relationship among $H_{rbc}$, $Q_b$, $Q_p$, and not including the actual whole blood hematocrit value, expressed as follows:

$$H_b = \frac{H_{rbc}(Q_b - Q_p)}{Q_b}$$

3. A system according to claim 1
wherein the control command recirculates at least a portion of plasma constituent for mixing with whole blood conveyed into the separation device.

4. A system according to claim 3
wherein the control command recirculates at least a portion of plasma constituent at a rate $Q_{Recirc}$ to achieve a desired hematocrit $H_i$ for whole blood conveyed into the separation device.

5. A system according to claim 4
wherein $Q_{Recirc}$ is derived as follows:

$$Q_{Recirc} = \left[\frac{H_b}{H_i} - 1\right] \times Q_b.$$

6. A system according to claim 4
wherein $H_i$ is no greater than about 40%.

7. A system according to claim 4
wherein $H_i$ is about 32%.

8. A system according to claim 1
wherein the control command controls $H_b$.

9. A system according to claim 1
and further including an element that generates an output based, at least in part, upon $H_b$.

10. A system according to claim 9
wherein the output comprises a value η representing efficiency of separation in the separation device, where:

$$\eta = \frac{Q_p}{(1 - H_b)Q_b}$$

11. A system according to claim 1
wherein the controller derives $H_{rbc}$ according to the following relationship:

$$H_{rbc} = 1 - \left(\frac{\beta}{gA\kappa S_Y}(q_b - q_p)\right)^{\frac{1}{k+1}}$$

where:

$Q_b$ is inlet blood flow rate (cm$^3$/sec), which when converted to ml/min, corresponds with $Q_b$, $Q_p$ is measured plasma flow rate (in cm$^3$/sec), which, when converted to ml/min corresponds with $Q_p$, β is a shear rate dependent term, and $S_y$ is a red blood cell sedimentation coefficient (sec) and $\beta/S_y = 15.8 \times 10^6$ sec$^{-1}$, A is the area of the separation device (cm$^2$), g is the centrifugal acceleration (cm/sec$^2$), which is the radius of the separation device multiplied by the rate of rotation squared $\Omega^2$ (rad/sec$^2$), and k is a viscosity constant=0.625, and K is a viscosity constant based upon k and another viscosity constant α=4.5, where:

$$\kappa = \frac{k+2}{\alpha}\left[\frac{k+2}{k+1}\right]^{k+1} = 1.272.$$

12. A system according to claim 11
wherein the separation device is free of any sensor operable to measure the actual whole blood hematocrit value.

13. A system according to claim 1
wherein the inlet path is free of any sensor operable to measure the actual whole blood hematocrit value.

14. A blood processing method comprising the steps of
rotating a centrifugal separation device at a controlled rate of rotation, the separation device having an area A,
conveying whole blood having an actual whole blood hematocrit value into the separation device at a determinable rate $Q_b$ for separation into red blood cells and a plasma constituent, the red blood cells in the separation device having an actual red blood cell hematocrit value,
removing plasma constituent from the separation device at a determinable rate $Q_p$ at least in part while whole blood is conveyed into the separation device,
removing red blood cells from the separation device at least in part while whole blood is conveyed into the separation device and plasma is removed from the separation device,
deriving at least in part while whole blood is conveyed into the separation device and plasma and red blood cells are removed from the separation device a value $H_b$ representing an apparent hematocrit of whole blood entering the separation device and a value $H_{rbc}$ representing an apparent hematocrit of red blood cells within the separation device, where:

$$H_b = f(H_{rbc})$$

and where:

$$H_{rbc} = f(Q_b, Q_p, A, g, RBC)$$

where:

g represents a centrifugal acceleration factor based upon the controlled rate of rotation, and RBC represents at least one red blood cell dependent factor not including either the actual whole blood hematocrit value or the actual red blood cell hematocrit value, and generating a control command based, at least in part, upon $H_b$ at least in part while whole blood is conveyed into the separation device and plasma and red blood cells are removed from the separation device.

15. A method according to claim 14
wherein $H_b$ is derived based upon a relationship among $H_{rbc}$, $Q_b$, $Q_p$, and not including the actual whole blood hematocrit value, expressed as follows:

$$H_b = \frac{H_{rbc}(Q_b - Q_p)}{Q_b}$$

16. A method according to claim 14
wherein the control command recirculates at least a portion of plasma constituent for mixing with whole blood conveyed into the separation device.

17. A method according to claim 16
wherein the control command recirculates at least a portion of plasma constituent at a rate $Q_{Recirc}$ to achieve a desired hematocrit $H_i$ for whole blood conveyed into the separation device.

18. A method according to claim 17
wherein $Q_{Recirc}$ is derived as follows:

$$Q_{Recirc} = \left[\frac{H_b}{H_i} - 1\right] \times Q_b.$$

19. A method according to claim 17
wherein $H_i$ is no greater than about 40%.

20. A method according to claim 17
wherein $H_i$ is about 32%.

21. A method according to claim 14
wherein the control command controls $Q_b$.

22. A method according to claim 14 and further the step of generating an output based, at least in part, upon $H_b$.

23. A method according to claim 22 wherein the output comprises a value η representing efficiency of separation in the separation device.

24. A method according to claim 14 wherein the value $H_{rbc}$ is derived as follows:

$$H_{rbc} = 1 - \left(\frac{\beta}{gA\kappa S_Y}(q_b - q_p)\right)^{\frac{1}{k+1}}$$

where:
- $q_b$ is inlet blood flow rate (cm³/sec), which when converted to ml/min, corresponds with $Q_b$,
- $q_p$ is measured plasma flow rate (in cm³/sec), which, when converted to ml/min corresponds with $Q_p$,
- β is a shear rate dependent term, and $S_y$ is a red blood cell sedimentation coefficient (sec) and $\beta/S_y = 15.8 \times 10^6$ sec⁻¹,
- A is the area of the separation device (cm²),
- g is the centrifugal acceleration (cm/sec²), which is the radius of the separation device multiplied by the rate of rotation squared $\Omega^2$ (rad/sec²), and
- k is a viscosity constant=0.625, and K is a viscosity constant based upon k and another viscosity constant α=4.5, where:

$$\kappa = \frac{k+2}{\alpha}\left[\frac{k+2}{k+1}\right]^{k+1} = 1.272.$$

25. A method according to claim 24 wherein the method is free of a step of using a sensor to measure the actual whole blood hematocrit value in the separation device.

26. A method according to claim 14 wherein the method is free of a step of using a sensor to measure the actual whole blood hematocrit value of blood conveyed into the separation device.

* * * * *